United States Patent [19]

Ertl

[11] Patent Number: 4,755,602

[45] Date of Patent: * Jul. 5, 1988

[54] PROCESS FOR PREPARING 1-OXA-3,8-DIAZA-4-OXO-SPIRO-[4,5]-DECANES

[75] Inventor: Josef Ertl, Wertingen, Fed. Rep. of Germany

[73] Assignee: Hoechst Aktiengesellschaft, Frankfurt am Main, Fed. Rep. of Germany

[ * ] Notice: The portion of the term of this patent subsequent to Aug. 25, 2004 has been disclaimed.

[21] Appl. No.: 883,096

[22] Filed: Jul. 8, 1986

[30] Foreign Application Priority Data

Jul. 10, 1985 [DE] Fed. Rep. of Germany ....... 3524541

[51] Int. Cl.$^4$ .......................................... C07D 498/10
[52] U.S. Cl. ......................................... 546/19; 524/99
[58] Field of Search ........................................ 546/19

[56] References Cited

U.S. PATENT DOCUMENTS 4,689,416 8/1987 Ertl et al. ............................... 546/19

FOREIGN PATENT DOCUMENTS

| 0079850 | 5/1983 | European Pat. Off. | 546/19 |
| 0095076 | 11/1983 | European Pat. Off. | 546/19 |
| 2933732 | 3/1981 | Fed. Rep. of Germany | 546/19 |
| 3149453 | 8/1982 | Fed. Rep. of Germany | 546/19 |
| 3217734 | 11/1983 | Fed. Rep. of Germany | 546/19 |
| 3408949 | 9/1984 | Fed. Rep. of Germany | 546/19 |
| 3523679 | 1/1986 | Fed. Rep. of Germany | 546/19 |

*Primary Examiner*—Robert T. Bond

[57] ABSTRACT

1-Oxa-3,8-diaza-4-oxo-spiro-[4,5]-decane compounds of the formula

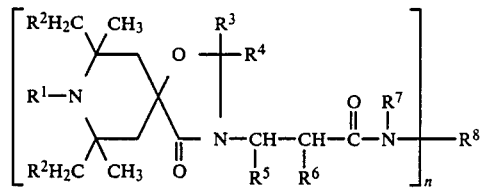

are new light stabilizers for protecting polymers from the damaging effect of UV radiation.

3 Claims, No Drawings

PROCESS FOR PREPARING 1-OXA-3,8-DIAZA-4-OXO-SPIRO-[4,5]-DECANES

The invention relates to new 1-oxa-3,8-diaza-4-oxo-spiro-[4,5]-decane compounds and to their preparation and use as light stabilizers for polymers or as intermediates for preparing plastic additives.

Compounds of the formula

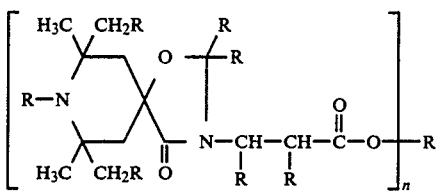

are known (cf. German Offenlegungsschrift No. 3,149,453). However, the process for their preparation is complicated since the reaction medium is changed several times during the reaction, and this involves additional extractions and distillations. Moreover, the compounds thus prepared are relatively volatile.

It has now been found that less volatile spirodecane compounds can be obtained in a simple process.

The invention thus provides 1-oxa-3,8-diaza-4-oxo-spiro-[4,5]-decane compounds of the formula I

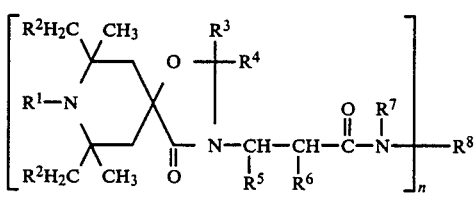

in which
n is 1 or 2,
$R^1$ is hydrogen, $C_1-C_4$-alkyl, benzyl, allyl, $C_2-C_{30}$-alkanoyl, $C_3-C_{20}$-alkenoyl, $C_7-C_{11}$-aroyl, $C_8-C_{14}$-arylalkanoyl or $C_8-C_{20}$-alkylaryl,
$R^2$ denotes hydrogen or $C_1-C_4$-alkyl,
$R^3$ is hydrogen, $C_1-C_{18}$-alkyl, $C_5-C_{12}$-cycloalkyl, a phenyl or naphthyl group which can be substituted by chlorine or $C_1-C_4$-alkyl, or a $C_7-C_{12}$-phenylalkyl group which can be substituted by $C_1-C_4$-alkyl,
$R^4$ denotes hydrogen, $C_1-C_4$-alkyl, $C_5-C_{12}$-cycloalkyl, $C_1-C_3$-alkenyl which is substituted by —COOH, carbo-$C_1-C_4$-alkoxy or carbamoyl, a phenyl, naphthyl or pyridyl group which can be substituted by $C_1-C_4$-alkoxy or $C_1-C_4$-alkyl, or a $C_7-C_{12}$-phenylalkyl group which can be substituted by $C_1-C_4$-alkyl or
$R^3$ and $R^4$ together with the carbon atom linking them form a cycloalkyl group which can be substituted by one to four $C_1-C_4$-alkyl groups, or a radical of the formula II

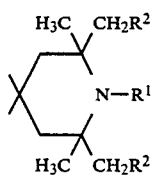

in which $R^1$ and $R^2$ have the abovementioned meaning,
$R^5$ is hydrogen, methyl, phenyl or carbo-$C_1-C_{21}$-alkoxy,
$R^6$ denotes hydrogen or methyl,
$R^7$ denotes hydrogen, $C_1-C_{10}$-alkyl or a radical of the formula III

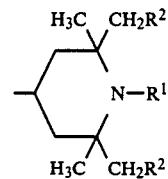

in which $R^1$ and $R^2$ have the abovementioned meaning,
$R^8$ in the case of n=1 denotes hydrogen, $C_1-C_{21}$-alkyl, $C_2-C_{22}$-alkenyl, $C_7-C_{18}$-phenylalkyl, $C_5-C_{12}$-cycloalkyl, phenyl, naphthyl, $C_7-C_{18}$-alkylphenyl, $C_2-C_{20}$-alkyl which is interrupted by —O— or

and/or can be substituted by a radical of the formula IV

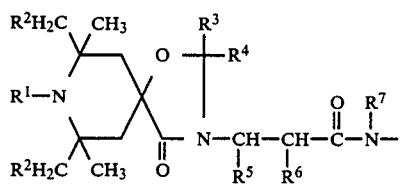

or by $C_1-C_{21}$-alkylcarboxyl, $R^1$, $R^2$, $R^3$, $R^4$, $R^5$, $R^6$ and $R^7$ haveing the abovementioned meaning and $R^9$ being hydrogen, $C_1-C_{10}$-alkyl or a radical of the formula III,
$R^8$ in the case of n=2 denotes straight-chain or branched $C_1-C_{30}$-alkylene, $C_6-C_{15}$-cycloalkylene, $C_2-C_{30}$-alkenylene or phenyldialkylene, it being possible for these radicals to be interrupted by —O— or

in which $R^9$ has the abovementioned meaning.
$R^1$ is preferably hydrogen, $C_1-C_4$-alkyl or $C_2-C_{18}$-alkanoyl, for example methyl, ethyl, propyl, butyl, acetyl, propionyl, butyryl, lauroyl or stearoyl, and particularly preferably hydrogen or one of the acid radicals mentioned. Especially, $R^1$ is hydrogen.
$R^2$ is preferably hydrogen or $C_1-C_4$-alkyl, for example methyl, ethyl, propyl or butyl. Especially, $R^2$ is hydrogen.
$R^3$ and $R^4$ independently of each other are $C_1-C_{18}$-alkyl, $C_5-C_{12}$-cycloalkyl or phenyl, for example, ethyl, butyl, octyl, lauryl, stearyl, cyclohexyl or cyclodecyl, and particularly preferably $C_1-C_7$-alkyl. Especially, $R^3$ and $R^4$ are $C_1-C_4$-alkyl, for example methyl.

$R^3$ and $R^4$, together with the carbon atom linking them, are preferably $C_5$-$C_{12}$-cycloalkylene, particularly preferably $C_6$- or $C_{12}$-cycloalkylene, and especially cyclododecylene.

$R^5$ is preferably hydrogen, methyl or phenyl, and particularly preferably hydrogen.

$R^6$ is preferably hydrogen or methyl. Especially, $R^6$ is hydrogen.

$R^7$ is preferably hydrogen or 2,2,4,4-tetramethylpiperid-4-yl.

$R^8$ is preferably $C_1$-$C_{21}$-alkyl, straight-chain or branched $C_1$-$C_{30}$-alkylene, for example methyl, ethyl, butyl, ethylene, butylene, hexylene, particularly preferably $C_2$-$C_{10}$-alkylene. Especially, $R^8$ is $C_2$-$C_6$-alkylene, for example hexylene.

The compounds according to the invention of the formula I are prepared by reacting compounds of the formula V $$\begin{array}{c} R^2H_2C\;\;CH_3 \quad R^3 \\ \diagdown\;\diagup \quad \quad \mid \\ \quad\quad\quad\quad O \;\text{---}\; R^4 \\ R^1\text{---}N \quad\quad\quad\quad\quad\quad\quad\quad O \\ \quad\quad\quad\quad\quad\quad\quad\quad\quad\quad\quad\quad \parallel \\ \diagup\;\diagdown\quad\quad\; N\text{---}CH\text{---}CH\text{---}C\text{---}OR' \\ R^2H_2C\;\;CH_3\;\; O \quad\quad \mid \quad\;\; \mid \\ \quad\quad\quad\quad\quad\quad\quad\quad\quad\;\; R^5 \;\;\;\; R^6 \end{array} \quad (V)$$

with amines of the formula VI $$\left[\begin{array}{c} R^7 \\ \diagdown \\ \quad N\text{---}R^8 \\ \diagup \\ H \end{array}\right]_n \quad (VI)$$

In these formulae n, $R^1$, $R^2$, $R^3$, $R^4$, $R^5$, $R^7$ and $R^8$ have the abovementioned meaning. $R'$ is $C_1$-$C_4$-alkyl, preferably methyl or ethyl. The compounds of the formula V can be obtained by reacting compounds of the formula VII $$\begin{array}{c} R^2H_2C\;\;CH_3 \quad R^3 \\ \diagdown\;\diagup \quad \quad \mid \\ \quad\quad\quad\quad O \;\text{---}\; R^4 \\ R^1\text{---}N \quad\quad\quad\quad\quad\quad\quad \mid \\ \quad\quad\quad\quad\quad\quad\quad\quad\quad\;\; \text{---}\; NH \\ \diagup\;\diagdown\quad\quad\quad\; \parallel \\ R^2H_2C\;\;CH_3\;\; O \end{array} \quad (VII)$$

with compounds of the formula VIII $$\begin{array}{c} \quad\quad\quad O \\ \quad\quad\quad \parallel \\ CH=C\text{---}C\text{---}O\text{---}R' \\ \mid \quad\;\; \mid \\ R^5 \quad R^6 \end{array} \quad (VIII)$$

where $R^1$, $R^2$, $R^3$, $R^4$, $R^5$, $R^6$ and $R'$ have the abovementioned meaning, at a temperature of 30° to 150° C. in the presence of a basic catalyst and in the presence of 0.05 to 20 mol %, relative to compound VII, of a phase transfer catalyst in an aromatic hydrocarbon which is liquid at room temperature, preferably toluene or xylene.

The phase transfer catalyst added is preferably a polyethylene glycol dialkyl ether, a substituted phosphonium salt, for example a tetraalkylphosphonium halide, or a substituted ammonium salt, for example tetraalkylammonium halide or trialkylbenzylammonium halide. In particular, triethylbenzylammonium chloride or tetraalkylphosphonium bromide is added. The amount is 0.05 to 20, preferably 0.1 to 10, in particular 1 to 10, mol % relative the compound of the formula VII.

The compound VIII is employed in an amount of 1 to 10, preferably 1 to 3, in particular 1 to 1.5, mol per 1 mol of compound VII.

The reaction is carried out in the presence of a basic catalyst. The basic catalyst used is an alkali metal, preferably sodium, which is employed in an amount of 1 to 30 mol %, preferably 2 to 10 mol %, relative to compound VII.

However, it is also possible to prepare the compounds of the formula I directly from the compounds of the formula VII by reacting the latter with a compound of the formula IX:

$$\left[\begin{array}{c} \quad\quad\quad O \quad R^7 \\ \quad\quad\quad \parallel \quad \mid \\ CH=C\text{---}C\text{---}N\;\text{---}\;R^8 \\ \mid \quad\;\; \mid \\ R^5 \quad R^6 \end{array}\right]_n \quad (IX)$$

n, $R^5$, $R^6$, $R^7$ and $R^8$ have the abovementioned meanings.

The reaction, as stated above, is carried out at a temperature of 30 to 150, preferably 50 to 120, in particular 70 to 120, °C. in the presence of an alkali metal, preferably sodium. The alkali metal is used in an amount of 1 to 30 mol %, preferably 2 to 10 mol %, relative to compound VII. Compound IX is used in an amount of 1 to 10, preferably 1 to 3, in particular 1 to 1.5, mol per one mol of compound VII.

Preference is given to reacting compounds of the formula V with compounds of the formula VI.

Suitable compounds of the formula VII are for example
2-butyl-7,7,9,9-tetramethyl-1-oxa-3,8-diaza-4-oxo-spiro-[4,5]-decane
2-iso-butyl-7,7,9,9-tetramethyl-1-oxa-3,8-diaza-4-oxo-spiro-[4,5]-decane
2-pentyl-7,7,9,9-tetramethyl-1-oxa-3,8-diaza-4-oxo-spiro-[4,5]-decane
2-isopentyl-7,7,9,9-tetramethyl-1-oxa-3,8-diaza-4-oxo-spiro-[4,5]-decane
2-hexyl-7,7,9,9-tetramethyl-1-oxa-3,8-diaza-4-oxo-spiro-[4,5]-decane
2-heptyl-7,7,9,9-tetramethyl-1-oxa-3,8-diaza-4-oxo-spiro-[4,5]-decane
2-isoheptyl-7,7,9,9-tetramethyl-1-oxa-3,8-diaza-4-oxo-spiro-[4,5]-decane
2-nonyl-7,7,9,9-tetramethyl-1-oxa-3,8-diaza-4-oxo-spiro-[4,5]-decane
2-isononyl-7,7,9,9-tetramethyl-1-oxa-3,8-diaza-4-oxo-spiro-[4,5]-decane
2-undecyl-7,7,9,9-tetramethyl-1-oxa-3,8-diaza-4-oxo-spiro-[4,5]-decane
2-phenyl-7,7,9,9-tetramethyl-1-oxa-3,8-diaza-4-oxo-spiro-[4,5]-decane
2-(4-chlorophenyl)-7,7,9,9-tetramethyl-1-oxa-3,8-diaza-4-oxospiro-[4,5]-decane
2-ethyl-2,7,7,9,9-pentamethyl-1-oxa-3,8-diaza-4-oxo-spiro-[4,5]-decane
2-propyl-2,7,7,9,9-pentamethyl-1-oxa-3,8-diaza-4-oxo-spiro-[4,5]-decane 2-isopropyl-2,7,7,9,9-pentamethyl-1-oxa-3,8-diaza-4-oxo-spiro-[4,5]-decane
2-butyl-2,7,7,9,9-pentamethyl-1-oxa-3,8-diaza-4-oxo-spiro-[4,5]-decane
2-isobutyl-2,7,7,9,9-pentamethyl-1-oxa-3,8-diaza-4-oxo-spiro-[4,5]-decane
2-pentyl-2,7,7,9,9-pentamethyl-1-oxa-3,8-diaza-4-oxo-spiro-[4,5]-decane
2-hexyl-2,7,7,9,9-pentamethyl-1-oxa-3,8-diaza-4-oxo-spiro-[4,5]-decane
2-nonyl-2,7,7,9,9-pentamethyl-1-oxa-3,8-diaza-4-oxo-spiro-[4,5]-decane
2,2,7,7,9,9-hexamethyl-1-oxa-3,8-diaza-4-oxo-spiro-[4,5]-decane
2,2,7,7,8,9,9-heptamethyl-1-oxa-3,8-diaza-4-oxo-spiro-[4,5]-decane
2,2-diethyl-7,7,9,9-tetramethyl-1-oxa-3,8-diaza-4-oxo-spiro-[4,5]-decane
2,2-dipropyl-7,7,9,9-tetramethyl-1-oxa-3,8-diaza-4-oxo-spiro-[4,5]-decane
2,2-dibutyl-7,7,9,9-tetramethyl-1-oxa-3,8-diaza-4-oxo-spiro-[4,5]-decane
2-ethyl-2-pentyl-7,7,9,9-tetramethyl-1-oxa-3,8-diaza-4-oxo-spiro-[4,5]-decane
2,2-dibenzyl-7,7,9,9-tetramethyl-1-oxa-3,8-diaza-4-oxo-spiro-[4,5]-decane
2,2,4,4-tetramethyl-7-oxa-3,13-diaza-14-oxo-dispiro-[5,1,4,2]-tetradecane
2,2,4,4-tetramethyl-7-oxa-3,14-diaza-15,oxo-dispiro-[5,1,5,2]-pentadecane
2,2,4,4-tetramethyl-7-oxa-3,20-diaza-21-oxo-dispiro-[5,1,11,2]-heneicosane
2,2,7,7,9,9-hexamethyl-1-oxa-3,8-diaza-4-oxo-8-acetyl-spiro-[4,5]-decane
2,2,4,4-tetramethyl-7-oxa-3,14-diaza-15-oxo-3-acetyl-dispiro-[5,1,5,2]-pentadecane
2,2,4,4-tetramethyl-7-oxa-3,20-diaza-21-oxo-3-acetyl-dispiro-[5,1,11,2]-heneicosane.

Examples of compounds of the formula VI are:
N-(2,2,6,6-tetramethyl-4-piperidyl)-3-methoxypropylamine
N-(2,2,6,6-tetramethyl-4-piperidyl)-3-ethoxypropylamine
N-(2,2,6,6-tetramethyl-4-piperidyl)-3-octadecyloxypropylamine
N-(2,2,6,6-tetramethyl-4-piperidyl)-3-dimethylaminopropylamine
N-(2,2,6,6-tetramethyl-4-piperidyl)-2-dimethylaminoethylamine
N-(2,2,6,6-tetramethyl-4-piperidyl)-4-diethylaminobutylamine
N-(2,2,6,6-tetramethyl-4-piperidyl)-aminopropan-3-ol
N-(2,2,6,6-tetramethyl-4-piperidyl)-4-diethylamino-1-methylbutylamine
2,2,6,6-tetramethyl-4-aminopiperidine
N-(2,2,6,6-tetramethyl-4-piperidyl)-butylamine
N-(2,2,6,6-tetramethyl-4-piperidyl)-octadecylamine
N-(2,2,6,6-tetramethyl-4-piperidyl)-cyclododecylamine
N-(2,2,6,6-tetramethyl-4-piperidyl)-hexylamine
Di-(2,2,6,6-tetramethyl-4-piperidyl)-amine
ammonia, butylamine, dicyclohexylamine, cyclododecylamine, hexylamine, dodecylamine, octadecylamine, dioctadecylamine, 2,3-dimethylcyclohexylamine, 2,6-dimethylmorpholine, methylcyclohexylamine, pyrrolidine, piperidine, 3,5,5-trimethylhexylamine, 2,2-dimethylpropylamine, di-n-octylamine, ethylenediamine, propylenediamine, 1,6-diaminohexane, 1,8-diaminooctane, 1,12-diaminodecane, 1,2-diaminopropane, 2,5-diamino-2,5-dimethylhexane, p-phenylenediamine, 1,8-diamino-p-menthane,
1,3-bis-(aminomethyl)-cyclohexane, 4,4'-diaminodicyclohexylmethane, 3,3'-dimethyl-4,4'-diaminodicyclohexylmethane, 4,4'-diaminodiphenylmethane, 2 (3), 5 (6)-bis-(aminomethyl)-norbornane mixed isomers, 3 (4), 8 (9)-bis-(aminomethyl)-tricyclo-[5.2.1.0$^{2,6}$]decane mixed isomers, bis-(3-aminopropyl)-piperazine,
4,7-dioxadecane-1,10-diamine, 4,9-dioxadodecane-1,12-diamine, 7-methyl-4,10-dioxatridecane-1,13-diamine;
3-amino-1-methylaminopropane, 3-amino-1-cyclohexylaminopropane,
3-amino-1-(2-ethyl)-hexylaminopropane, N-(cyclohexyl)-ethylenediamine, N-(cyclohexyl)-1,6-diaminohexane, N-(2-hydroxypropyl)-ethylenediamine,
N-(2,2,6,6-tetramethyl-4-piperidyl)-ethylenediamine
N-(2,2,6,6-tetramethyl-4-piperidyl)-1,6-diaminohexane
N-(2,2,6,6-tetramethyl-4-piperidyl)-1,3-bis-(aminomethyl)-cyclohexane,
N-(2,2,6,6-tetramethyl-4-piperidyl)-3(4), 8(9)-bis-(aminomethyl)-tricyclo-[5.2.1.0$^{2,6}$]-decane mixed isomers;
N,N'-bis-(2,2,6,6-tetramethyl-4-piperidyl)-ethylenediamine
N,N'-bis-(2,2,6,6-tetramethyl-4-piperidyl)-1,6-diaminohexane
N,N'-bis-(2,2,6,6-tetramethyl-4-piperidyl)-3(4), 8(9)-bis-(aminomethyl)-tricyclo-[5.2.1.0$^{2,6}$]-decane mixed isomers
N,N'-bis-(2,2,6,6-tetramethyl-4-piperidyl)-1,3-bis-(aminomethyl)-cyclohexane,
N,N'-bis-(2,2,6,6-tetramethyl-4-piperidyl)-4,9-dioxadodecane-1,12-diamine,
N,N'-bis-cyclododecyl-1,6-diaminohexane,
N,N'-bis-isopropyl-1,6-diaminohexane,
N,N'-bis-cyclohexyl-1,6-diaminohexane,
N,N'-bis-(2,2,6,6-tetramethyl-4-piperidyl)4,4'-diaminodicyclohexylmethane,
N-(2,2,6,6-tetramethyl-4-piperidyl)-N'-(cyclododecyl)-1,6-diaminohexane, Suitable compounds of the formula VIII are for example
methyl acrylate
ethyl acrylate
butyl acrylate
methyl methacrylate
ethyl methacrylate
butyl methacrylate
methyl crotonate
ethyl crotonate
Suitable compounds of the formula IX are for example acrylamide
methacrylamide
N,N'-methylene-bis-(acrylamide)
N,N'-ethylene-bis-(acrylamide)
N,N'-hexamethylene-bis-(acrylamide)
glyoxal-bis-(acrylamide)
N-(2,2,6,6-tetramethylpiperid-4-yl)-acrylamide
N-(2,2,6,6-tetramethylpiperid-4-yl)-crotonamide
N-(2,2,6,6-tetramethylpiperid-4-yl)-methacrylamide
N,N'-bis-(2,2,6,6-tetramethylpiperid-4-yl)-N,N'-ethylene-bis-(acrylamide)
N,N'-bis-(2,2,6,6-tetramethylpiperid-4-yl)-N,N'-hexamethylene-bis-(acrylamide)

The compounds according to the invention of the formula I compared with the compounds of German Offenlegungsschrift No. 3,149,453, have surprisingly better properties which are of critical importance for their use as light stabilizers for polymers.

The incorporation of the stabilizers into polymers and the processing of these stabilized polymers are significantly affected by the volatility and thermostability. Surprisingly, the compounds according to the invention are significantly less volatile than the compounds of German Offenlegungsschrift No. 3,149,453.

The compounds according to the invention of formula I are used above all as light stabilizers, for example for polyolefins, in particular polyethylene and polypropylene, ethylene/propylene copolymers, polybutylene, and also polystyrene, chlorinated polyethylene as well as polyvinyl chloride, polyester, polycarbonate, polymethyl methacrylates, polyphenylene oxides, polyamides, polyurethanes, polypropylene oxide, polyacetals, phenol-formaldehyde resins, epoxide resins, polyacrylonitrile and corresponding copolymers, and also ABS terpolymers. Preferably, the compounds prepared according to the invention are used for stabilizing polypropylene, low-molecular and high-molecular polyethylene, ethylene-propylene copolymers, polyvinyl chloride, polyester, polyamide, polyurethanes, polyacrylonitrile, ABS, terpolymers of acrylates, styrene and acrylonitrile, copolymers of styrene and acrylonitrile or styrene and butadiene, in particular for polypropylene, polyethylene, ethylene-propylene copolymers or ABS.

The compounds according to the invention can also be used for stabilizing natural materials, for example rubber, and also for lubricating oils. They are also suitable for stabilizing surface coatings.

The surface coatings can be of any types used in industrial surface-coating, preferably baking finishes. The latter are baked at an elevated temperature, in order to obtain optimum properties. Preference is given to wet surface coatings which contain as the binder: combinations of oil-modified polyester resins (oil alkyd resins) and melamine/formaldehyde resins or combinations of non-self-crosslinking polyacrylate resins and melamine/formaldehyde resins or combinations of saturated polyesters and melamine/formaldehyde resins or self-crosslinking polyacrylate resins, or polyacrylate resins with copolymerized styrene. Two-component acrylate resin coatings, composed of acrylate resin containing hydroxyl groups and aliphatic or aromatic isocyanates, as well as thermoplastic polyacrylate resin coatings should also be mentioned. In addition, two-component polyurethane resin coatings, composed of polyester resins containing hydroxyl groups and/or polyether resins, hardened with aliphatic or aromatic isocyanates are also to be mentioned. For metalized coatings, thermoplastic polyacrylate resins or non-self-crosslinking polyacrylate resins in combination with butanol-etherified melamine resins and also polyacrylate resins containing hydroxyl groups and hardened with aliphatic isocyanates, are of particular importance. Powder coatings which are known per se and which have been treated, for example, with a solution of the compounds according to the invention, are also included.

The compounds according to the invention are incorporated in the materials which are to be protected by methods known per se, and it is also possible to equip monomers, prepolymers or precondensates with these stabilizers.

In addition to the compounds of the formula (I), further compounds can also be added to the plastics.

Examples of such other compounds are antioxidants based on sterically hindered phenols, costabilizers containing sulfur or phosphorus, or a mixture of suitable sterically hindered phenols and sulfur- and/or phosphorus-containing compounds. Such compounds are, for example, benzofuran-2-one and/or indolin-2-one compounds, sterically hindered phenols such as stearyl β-(4-hydroxy-3,5-di-t-butylphenyl)-propionate, methane tetrakis-[methylene-3-(3',5'-di-t-butyl-4-hydroxyphenyl)-propionate], 1,3,3-tris-(2-methyl-4-hydroxy-5-t-butylphenyl)-butane, 1,3,5-tris-(4-t-butyl-3-hydroxy-2,6-dimethylbenzyl)-1,3,5-triazine-2,4,6-(1H, 3H, 5H)-trione, bis-(4-t-butyl-3-hydroxy-2,6-dimethylbenzyl)dithiolterephthalate, tris-(3,5-t-butyl-4-hydroxybenzyl)isocyanurate, the triester of β-(4-hydroxy-3,5-di-t-butylphenyl)-propionic acid with 1,3,5-tris-(2-hydroxyethyl)-s-triazine-2,4,6-(1H, 3H, 5H)-trione, glycol bis-[3,3-bis-(4'-hydroxy-3-t-butylphenyl)-butanoate], 2,3,5-trimethyl-2,4,6-tris-(3,5-di-t-butyl-4-hydroxybenzyl)-benzene, 2,2'-methylene-bis-(4-methyl-6-t-butylphenyl)-terephthalate, 4,4'-methylene-bis-(2,6-di-t-butylphenol), 4,4'-butylidene-bis-(t-butyl-meta-cresol), 4,4-thio-bis-(2-t-butyl-5-methylphenol) and 2,2'-methylene-bis-(4-methyl-6-t-butylphenol). Costabilizers having an antioxidant action can also be added, such as, for example, sulfur-containing compounds, for example distearyl thiodipropionate, dilauryl thiodipropionate, methane tetrakis-(methylene-3-hexyl-thiopropionate), methane tetrakis-(methylene-3-dodecyl-thiopropionate) and dioctadecyl disulfide, or phosphorus-containing compounds such as, for example, trinonylphenyl phosphite; 4,9-distearyl-3,5,8,10-tetraoxadiphosphaspiro-undecane, tris-(2,4,-t-butylphenyl)phosphite or tetrakis(2,4-di-t-butylphenyl)-4,4'-biphenylene-diphosphonite.

The compounds of the formula I and their abovementioned mixtures can also be used in the presence of further additives. Such additives are known per se and belong, for example, to the group of aminoacrylic compounds, UV-absorbers and light stabilizers, such as 2-(2'-hydroxyphenyl)-benzotriazoles, 2-hydroxybenzophenones, 1,3-bis-(2'-hydroxybenzoyl)-benzenes, salicylates, cinnamates, esters of substituted or unsubstituted benzoic acids, sterically hindered amines and oxalic acid diamides.

The compounds according to the invention of the formula I are used in amounts of 0.01–5% by weight in the case of plastics, 20 to 80% by weight in the case of stabilizer concentrates and 0.02–5% by weight in the case of surface coatings.

The examples below serve to illustrate the invention.

EXAMPLE 1

45.0 g (0.1 mol) of methyl 2,2,4,4-tetramethyl-7-oxa-3,20-diaza-21-oxo-dispiro[5,1,11,2]-heneicos-20-ylpropanate were added to 150 g of xylene and dried under a water separator. To this were added 0.4 g of tetraethylphosphonium bromide, 5.8 g (0.05 mol) of hexamethylenediamine and 0.1 g of sodium hydride. Almost 3.2 g (0.1 mol) of methanol were distilled off via a column in 24 h. After cooling down, the precipitate was filtered off with suction. Recrystallization from toluene gave a colorless product having a melting point of 179° C.

EXAMPLE 2

36.4 g (0.1 mol) of 2,2,4,4-tetramethyl-7-oxa-3,20-diaza-21-oxo-dispiro-[5,2,11,2]-heneicosane were presented in 100 g of toluene and dried under a water separator. At 80° C. 0.4 g of triethylbenzylammonium chloride, 2.0 g of sodium and 11.2 g (0.05 mol) of N,N'-methylene-bis(acrylamide) were then added, and the batch was stirred at 90° C. for 14 h. The precipitate was filtered off with suction at room temperature and recrystallized from toluene. This gave a colorless product having a melting point of 148° C.

I claim:

1. A process for preparing a 1-oxa-3,8-diaza-4-oxo-spiro-[4,5]-decane compound of the formula I

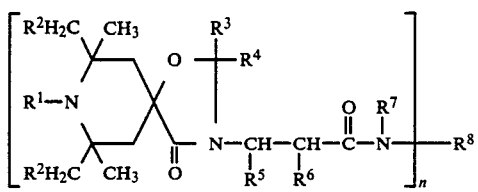

in which n is 1 or 2

$R^1$ is hydrogen, $C_1$–$C_4$-alkyl, benzyl, allyl, $C_2$–$C_{30}$-alkanoyl, $C_3$–$C_{20}$-alkenoyl, $C_7$–$C_{11}$-aroyl, $C_8$–$C_{14}$-arylalkanoyl or $C_8$–$C_{20}$-alkylaryl, $R^2$ denotes hydrogen or $C_1$–$C_4$-alkyl, $R^3$ is hydrogen, $C_1$–$C_{18}$-alkyl, $C_5$–$C_{12}$-cycloalkyl, a phenyl or naphthyl group which can be substituted by chlorine or $C_1$–$C_4$-alkyl, or a $C_7$–$C_{12}$-phenylalkyl group which can be substituted by $C_1$–$C_4$-alkyl, $R^4$ denotes hydrogen, $C_1$–$C_4$-alkyl, $C_5$–$C_{12}$-cycloalkyl, $C_1$–$C_3$-alkenyl which is substituted by —COOH, carbo-$C_1$–$C_4$-alkoxy or carbamoyl, a phenyl, naphthyl or pyridyl group which can be substituted by $C_1$–$C_4$-alkoxy or $C_1$–$C_4$-alkyl, or a $C_7$–$C_{12}$-phenylalkyl group which can be substituted by $C_1$–$C_4$-alkyl or $R^3$ and $R^4$ together with the carbon atom linking them form a cycloalkyl group which can be substituted by one to four $C_1$–$C_4$-alkyl groups, or a radical of the formula II

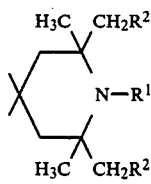

in which $R^1$ and $R^2$ have the abovementioned meaning, $R^5$ is hydrogen, methyl, phenyl or carbo-$C_1$–$C_{21}$-alkoxy, $R^6$ denotes hydrogen or methyl, $R^7$ denotes hydrogen, $C_1$–$C_{10}$-alkyl or a radical of the formula III

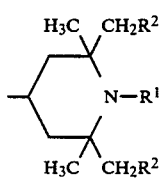

in which $R^1$ and $R^2$ have the abovementioned meaning, $R^8$ in the case of n=1 denotes hydrogen, $C_1$–$C_{21}$-alkyl, $C_2$–$C_{22}$-alkenyl, $C_7$–$C_{18}$-phenylalkyl, $C_5$–$C_{12}$-cycloalkyl, phenyl, naphthyl, $C_7$–$C_{18}$-alkylphenyl, $C_2$–$C_{20}$-alkyl which is interrupted by —O— or

and/or can be substituted by a radical of the formula IV

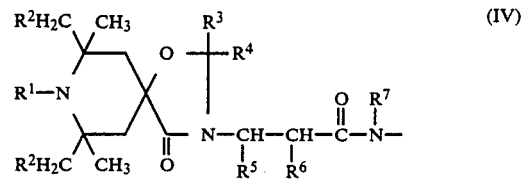

or by $C_1$–$C_{21}$-alkylcarboxyl, $R^1$, $R^2$, $R^3$, $R^4$, $R^5$, $R^6$ and $R^7$ haveing the abovementioned meaning and $R^9$ being hydrogen, $C_1$–$C_{10}$-alkyl or a radical of the formula III, $R^8$ in the case of n=2 denotes straight-chain or branched $C_1$–$C_{30}$-alkylene, $C_6$–$C_{15}$-cycloalkylene, $C_2$–$C_{30}$-alkenylene or phenyldialkylene, it being possible for these radicals to be interrupted by —O— or

in which $R^9$ has the abovementioned meaning, by reacting a 1-oxa-3,8-diaza-4-oxo-spiro-[4,5]-decane compound with a γ, δ-unsaturated compound in an inert solvent at a temperature of 30° to 150° C. in the presence of a basic catalyst, which comprises reacting compounds of the formula VII

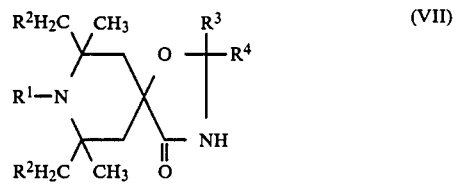

in which $R^1$, $R^2$, $R^3$ and $R^4$ have the abovementioned meanings either (a) first with compounds of the formula VIII

in which $R^5$ and $R^6$ have the abovementioned meanings and R' is $C_1$–$C_4$-alkyl, in the presence of 0.05 to 20 mol %, relative to compound VII, of a phase transfer catalyst, which phase catalyst is a substituted ammonium or phosphonium salt or a polyethylene glycol dialkyl ether, in an aromatic hydrocarbon which is liquid at room temperature, and then the reaction products of the formula V

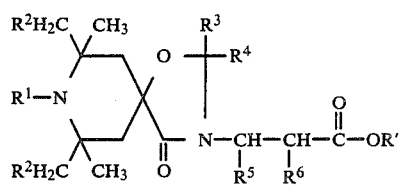 (V)

in which $R^1$, $R^2$, $R^3$, $R^4$, $R^5$, $R^6$ and $R'$ have the above-mentioned meanings, in the same solvent and at the same temperature with compounds of the formula VI

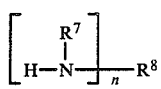 (VI)

in which n, $R^7$ and $R^8$ have the above-mentioned meanings, or (b) with compounds of the formula IX

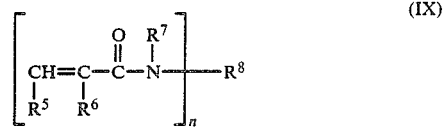 (IX)

in which n, $R^5$, $R^6$, $R^7$ and $R^8$ have the abovementioned meanings in the presence of 0.05 to 20 mol %, relative to compound VII, of a said phase transfer catalyst in an aromatic hydrocarbon which is liquid at room temperature.

2. The process as claimed in claim 1, wherein said phase transfer catalyst is a tetraalkylammonium or trialkylbenzylammonium chloride.

3. The process as claimed in claim 1 wherein said phase transfer catalyst is a tetraalkylphosphonium bromide.

* * * * *